(12) United States Patent
McLoone (10) Patent No.: US 11,109,987 B2
(45) Date of Patent: Sep. 7, 2021

(54) VACUUM DEVICE FOR A PROSTHETIC (71) Applicant: Anclote Manufacturing Company, Inc., Largo, FL (US)

(72) Inventor: Kevin McLoone, Largo, FL (US)

(73) Assignee: Anclote Manufacturing Company, Inc., Largo, FL (US)

( * ) Notice: Subject to any disclaimer, the term of this patent is extended or adjusted under 35 U.S.C. 154(b) by 0 days.

(21) Appl. No.: 16/803,437

(22) Filed: Feb. 27, 2020

(65) Prior Publication Data

US 2020/0276033 A1 Sep. 3, 2020

Related U.S. Application Data (60) Provisional application No. 62/812,464, filed on Mar. 1, 2019.

(51) Int. Cl.
*A61F 2/80* (2006.01)
*A61F 2/60* (2006.01)
A61F 2/78 (2006.01)

(52) U.S. Cl.
CPC .............. *A61F 2/80* (2013.01); *A61F 2/60* (2013.01); *A61F 2002/7875* (2013.01); *A61F 2002/805* (2013.01); *A61F 2002/807* (2013.01)

(58) Field of Classification Search
CPC ........ A61F 2/60; A61F 2/80; A61F 2002/805; A61F 2002/807; A61F 2002/7875
See application file for complete search history.

(56) References Cited

U.S. PATENT DOCUMENTS

| 6,287,345 B1 * | 9/2001 | Slemker | A61F 2/80 |
| | | | 623/34 |
| 6,554,868 B1 | 4/2003 | Caspers | |
| 7,468,079 B2 | 12/2008 | Collier | |

(Continued)

FOREIGN PATENT DOCUMENTS

| CN | 2360516 Y | 1/2000 |
| CN | 103625826 A | 3/2014 |

OTHER PUBLICATIONS

International Search Report and Written Opinion, dated Apr. 30, 2020, for International Application No. PCT/US2020/020390 from the.

(Continued)

*Primary Examiner* — Bruce E Snow
(74) *Attorney, Agent, or Firm* — Burr & Forman LLP; Patrick A. Reid (57) ABSTRACT The Prosthetic Vacuum Pump is a manually-operated device, that is affixed to or integral with a prosthetic socket. The manual operation allows a wearer to increase the vacuum in the socket cavity if there is any noticeable decrease at any time. The Prosthetic Vacuum Pump includes a removable pump mechanism that allows a user to customize the level of vacuum drawn by the Prosthetic Vacuum Pump. The intake valve of the Prosthetic Vacuum Pump is in direct connection with the cavity of a prosthetic socket. By eliminating vacuum lines, the vacuum pump creates an immediate vacuum in the cavity. The result is an immediate suspension when the prosthetic limb is put on without the need to walk or wait for the battery to draw a sufficient vacuum. The compact construction and optional depress-lock is easily hidden beneath clothing.

13 Claims, 5 Drawing Sheets (56) References Cited

U.S. PATENT DOCUMENTS

| | | |
|---|---|---|
| 7,744,653 B2 | 6/2010 | Rush et al. |
| 8,211,187 B2 | 7/2012 | Slemker et al. |
| 9,364,348 B2 | 6/2016 | Sandahl |
| 9,775,715 B2 | 10/2017 | Boiten |
| 2005/0131550 A1* | 6/2005 | Coop ................. A61F 2/80 623/36 |
| 2007/0168045 A1* | 7/2007 | Slemker ............ B29C 70/446 623/34 |
| 2008/0086218 A1 | 4/2008 | Egilsson |
| 2008/0221705 A1 | 11/2008 | Scussel |
| 2013/0282143 A1 | 10/2013 | Perkins et al. |
| 2016/0058583 A1* | 3/2016 | Hines ................. A61F 2/80 623/34 |
| 2018/0036149 A1 | 2/2018 | Harris et al. |
| 2018/0055661 A1 | 3/2018 | Erdmann et al. |
| 2018/0153715 A1 | 6/2018 | Jonsson et al. |
| 2019/0008663 A1 | 1/2019 | Cheng et al. |

OTHER PUBLICATIONS

Optimization of vacuum pump device for use in rapid fitment of prosthetic limbs, MIT Libraries, DSpace@MIT, Garcia, Phillip Thomas, Jun. 2008.

* cited by examiner

VACUUM DEVICE FOR A PROSTHETIC

CROSS-REFERENCE TO RELATED APPLICATION

The application claims the benefit of U.S. Provisional Patent Application No. 62/812,464 titled Device for Creating an Elevated Vacuum in a Prosthetic, filed on Mar. 1, 2019.

FIELD

The present disclosure relates to a prosthetic device for individuals that have had an amputation of one of their limbs and more particularly to a device that creates an elevated vacuum in the socket of a prosthesis to secure a prosthetic to a residual limb.

BACKGROUND

A prosthetic limb often replaces an amputated portion of a limb or extremity. The prosthesis helps an amputee regain the use or function of a lost limb or extremity. Historically, prosthetic limbs have been made of various types of rigid materials (e.g. wood, metal, and plastics).

Prosthetic limbs may be attached to the residual limb in various ways. Prosthetic limbs may be suspended from a user's body by a pulley, belt, or strap suspension. Other methods include mechanical or electric pumps to establish negative pressures. However, many of these systems look unnatural, are heavy, and are often difficult to use or adjust. Furthermore, these systems may pull constant negative pressures that are so forceful that they can be uncomfortable or cause damage to the residual limb tissue.

Another problem with existing mechanical vacuum suspension methods is that change in volume of the residual limb is not compensated for with the settings of those mechanical systems, requiring the user to set an appointment and see their prosthetist for an adjustment of the pump or the socket. When an amputee is wearing a prosthesis, especially one for a leg or lower extremity, there is increased pressure on the residual limb and constant pistoning inherently taking place from the weight of the prosthetic limb from toe off to heel strike pulling on the tissue of the residual limb, which causes the loss of fluids within the residual limb. The loss of fluids leads to a decrease in volume of the residual limb during the day. In these instances, an amputee may compensate for this by changing into thicker socks throughout the day. This is a cumbersome practice as it requires removing the prosthesis several times and even in public places.

Some vacuum pump methods utilize the weight of a user to engage the pump. In the weight-activated vacuum pumps, each step by the wearer causes the weight-activated pump to draw a small amount of air out of the socket cavity. However, each step of the wearer will not be identical in pressure or stability. This is because each residual limb may have different problems or configurations, such as, volume, shape, presence of scar tissue, skin graft, bone prominence, uneven limb volume, neuroma, pain, edema, or soft tissue configuration. Additionally, individual variation of weight and balance in each step applies a different amount of pressure to the pump. This may lead to the vacuum being too high and causing pain and discomfort, or being too low and resulting in loosening of the socket with respect to the residual limb throughout the day. Weight activated pumps also cannot be used with prosthetics on upper extremities.

Another attempted solution to this problem is a battery operated pump attached to a prosthesis. In battery-operated vacuum pumps, the batteries will need to be charged regularly or replaced. The wearer may fail to charge the batteries or be in a situation where charging the batteries is not feasible. Batteries also wear out over time, which can lead to the wearer being caught off guard with no way to suspend his or her prosthesis. Electronic vacuum pumps also create a noise when operating, which can cause distractions or embarrassment for the user.

There is a need for a manually-operated prosthesis with a vacuum pump that is compact, creates an elevated vacuum in a socket cavity, provides improved control over the vacuum in the socket cavity, and is easily used throughout the day to adjust the vacuum as needed.

SUMMARY

In one embodiment, the Prosthetic Vacuum Pump creates an elevated vacuum in a prosthetic socket, with a suspension sleeve creating a seal to the residual limb, or a liner interface with an external seal creating a seal to the inside socket wall. The vacuum pump has a body with an inner chamber that is open at one end. A prosthetic socket is affixed to and extends upward from the body. When the body is attached to the socket, the inner chamber is in fluid communication with the prosthetic socket via an intake port located on a top surface of the body. A pump mechanism is configured to securely insert into the inner chamber. A first end of a piston extends out of a first end of the pump mechanism and into the inner chamber. A second end of the piston is exposed or extends out from a second end of the pump mechanism so that a user may press or pull the second end of the piston to reciprocate the first end of the piston within the inner chamber to draw air out of the prosthetic socket.

In another exemplary embodiment, the pump mechanism includes a plunger and a spring; the plunger may be attached to the second end of the piston and extends outward from the second end of the pump mechanism; and the spring is located between the plunger and the first end of the pump mechanism such that after the piston moves in a first direction within the chamber, the spring moves the piston in a second direction. The pump mechanism may also be set to a predetermined level of vacuum or amount of volume to draw from the socket on each full reciprocation of the piston within the chamber.

In another exemplary embodiment, an intake valve is located on a top surface of the body in the distal end of the prosthetic socket and air is drawn out of the prosthetic socket through the intake valve and into the inner chamber.

In another exemplary embodiment, the vacuum pump includes a locking mechanism to secure the piston in a depressed position for a lower profile. The locking mechanism may be a locking pin and a locking slot.

In another exemplary embodiment, the body may be affixed to a distal end of the prosthetic socket. The body may be affixed on the outside of the prosthetic socket provided that it retains fluid communication with the socket. Alternatively, the body may be integrally formed with or molded into a prosthetic socket.

In another exemplary embodiment, the vacuum pump may include a prosthetic appendage attached to the bottom of the body.

In another exemplary embodiment, the pump mechanism is removably attached and a user may employ different pump mechanisms with the same vacuum pump body. The different pump mechanisms may have a different predetermined level of vacuum.

In another exemplary embodiment, the inner chamber includes an exhaust port to release air from the inner chamber to atmosphere.

In another exemplary embodiment, an intake valve is located on the intake port to prevent back flow of air into the prosthetic socket maintaining the vacuum.

In another exemplary embodiment, a vacuum pump to create an elevated vacuum in a prosthetic socket includes a body having an inner chamber in fluid communication with a prosthetic socket and a pump mechanism configured to attach to the body within the inner chamber. The pump mechanism may include a plunger attached to a first end of a piston shaft and interacting with a first end of a spring. A second end of the spring may abut or interact with a flange or edge on a second end of the pump mechanism. A second end of the piston may extend out of a second end of the pump mechanism and into the inner chamber. The plunger may extend out of a first end of the pump mechanism so that a user may manually pull or press the plunger such that a first movement of the plunger moves the piston within the inner chamber expelling air out of the inner chamber and the spring causes a second movement of the piston drawing air out of the prosthetic socket and into the inner chamber creating the elevated vacuum.

In another exemplary embodiment, the predetermined level of vacuum drawn by the pump mechanism may be accomplished by a biasing member with different compression lengths, compression force, or different internal volume. By way of example, the pump mechanism may include a spring to bias the piston in a starting position. When the piston is moved in a first direction, by either pushing or pulling, and then released, the spring will return the piston to the starting position. In one embodiment, a user may employ different pump mechanisms where each pump mechanism, or cartridge, has a spring with a different spring constants. Alternatively, adjusting the predetermined level of vacuum may be accomplished by adjusting the starting position or depth of the plunger or piston within the pump mechanism.

In another exemplary embodiment, a vacuum pump to create an elevated vacuum in a prosthetic socket includes a body integrally attached to a distal end of the prosthetic socket, an inner chamber within the body and open at one end in direct fluid communication with the prosthetic socket, and a pump cartridge configured to be removably attached to the body by insertion in the inner chamber. The pump cartridge may include a spring and a piston with one end of the piston extending out of a first end of the pump cartridge such that a piston head on the first end of the piston extends into the inner chamber. A first end of the spring interacts with an internal side, edge, or flange on the first end of the pump cartridge and a second end of the spring interacts with the piston such that when the piston is manually displaced in a first direction, the spring is depressed or expanded. Then, when a user releases the push or pull, the spring will return to its neutral compressed or expanded state which moves the piston in a second direction to return the piston to a starting position. The movement of the piston head within the inner chamber draws air out of the prosthetic socket and expels air to atmosphere to create an elevated vacuum in the prosthetic socket.

DETAILED DESCRIPTION

Reference will now be made in detail to the following exemplary embodiments, which are illustrated in the accompanying drawings, wherein like reference numerals refer to like elements throughout. The exemplary embodiments may be embodied in various forms without being limited to the exemplary embodiments set forth herein. Descriptions of well-known parts are omitted for clarity.

Figure 1:
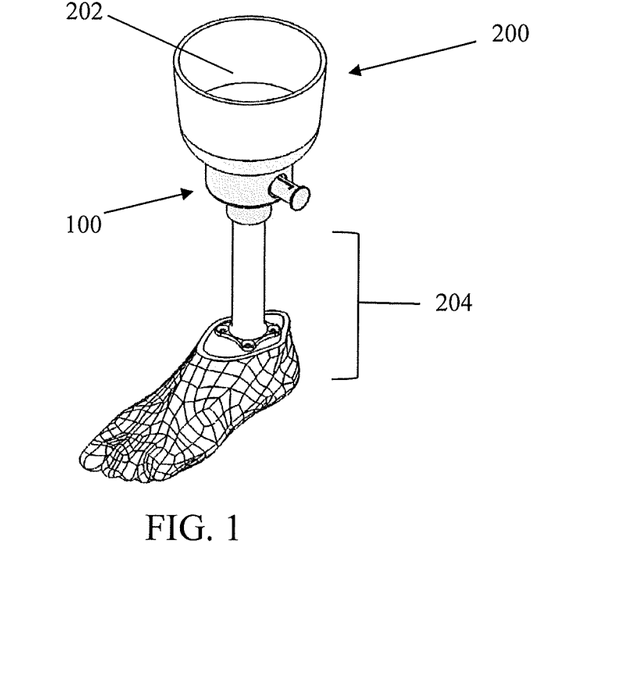
FIG. 1 is a perspective view of the Prosthetic Vacuum Pump on a prosthetic.

Referring to FIG. 1, the Prosthetic Vacuum Pump 100 is a low-profile assembly that may be affixed to or molded into the distal end of a prosthetic socket 200 and also attached to a prosthetic limb 204 resulting in a complete prosthetic. The Prosthetic Vacuum Pump 100 creates an elevated vacuum that secures a prosthetic socket 200 to a residual limb. Elevated vacuum suspension uses negative pressure that maintains limb volume resulting in the residual limb maintaining contact to the inner wall of a cavity 202 of the prosthetic socket 200 and conforming to the shape of the socket to provide a more comfortable and secure fit. Furthermore, the elevated vacuum resists the volume change of the residual limb that occurs when fluid is pushed away from the residual limb. In some embodiments, the Prosthetic Vacuum Pump 100 may be mounted onto the distal end of a prosthetic socket 200 to retrofit existing prosthetics. This may be done by screwing or bolting the Vacuum Pump 100 to the distal end of a prosthetic socket 200 and creating a hole in the prosthetic socket 200 that results in the intake port 106 (shown in FIG. 2) being in direct fluid communication with the cavity 202.

The Prosthetic Vacuum Pump 100 allows a user to manually create an elevated vacuum in a cavity 202 of the prosthetic socket 200. The Pump 100 may be in direct fluid communication with the prosthetic socket 200 to draw air directly out of the cavity 202 thereby securing the prosthetic socket 200 to a residual limb. The Pump 100 may be made of plastic, metal, or other rigid material to facilitate a secure connection with the materials of the socket 200.

Figure 2:
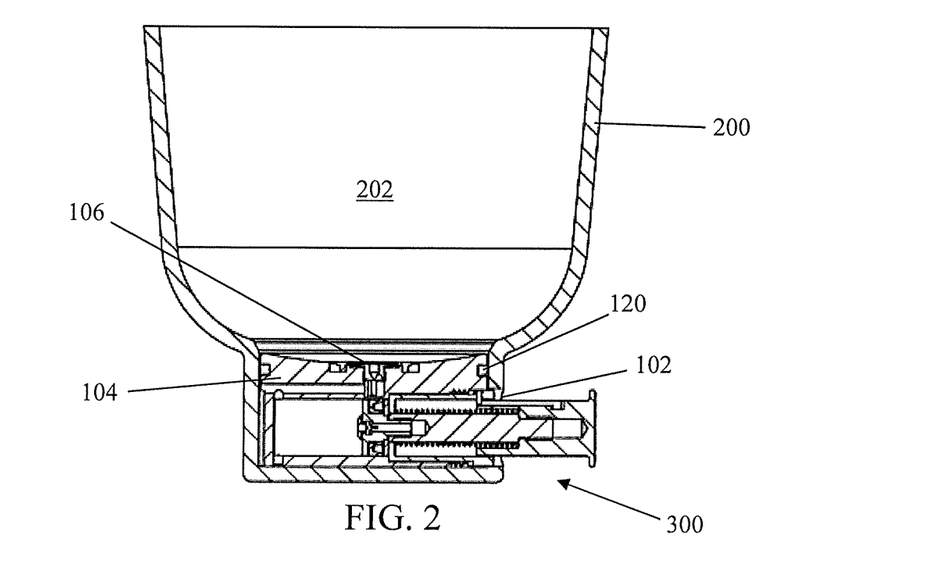
FIG. 2 illustrates a cross-sectional view of Prosthetic Vacuum Pump integrally molded into a prosthetic socket.

Referring to FIG. 2, a cross-section of the Pump 100 is shown molded into a prosthetic socket 200. In some exemplary embodiments, a removable pump mechanism 300, or pump cartridge, inserts or fastens into an opening 102 in the body 104 of the Prosthetic Vacuum Pump 100 and a sealing membrane 120 around the body 104 facilitates a more secure fit of the socket 200. In this configuration, the intake port 106 of the Pump 100 is in direct fluid communication with the cavity 202.

Figure 3:
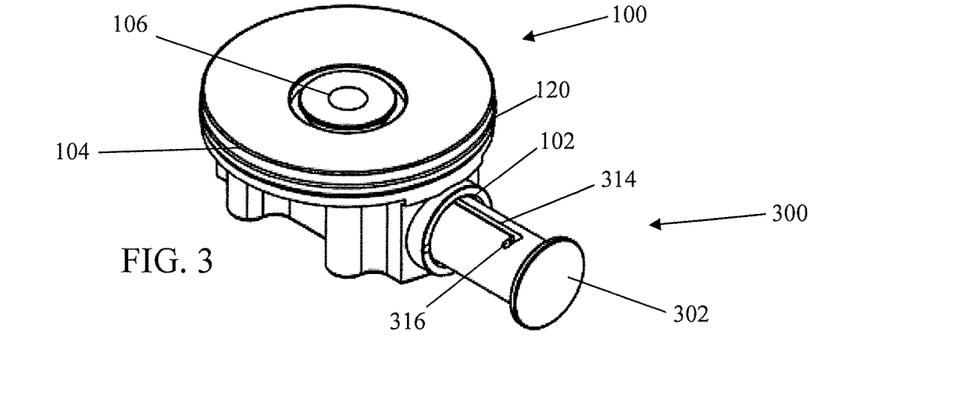
FIG. 3 is a perspective view of the Prosthetic Vacuum Pump.

Referring to FIG. 3, the Prosthetic Vacuum Pump 100 is shown apart from a prosthetic socket and limb. The pump mechanism 300 may be removably attached in the opening 102 by, for example, threaded fitting.

Figure 4:
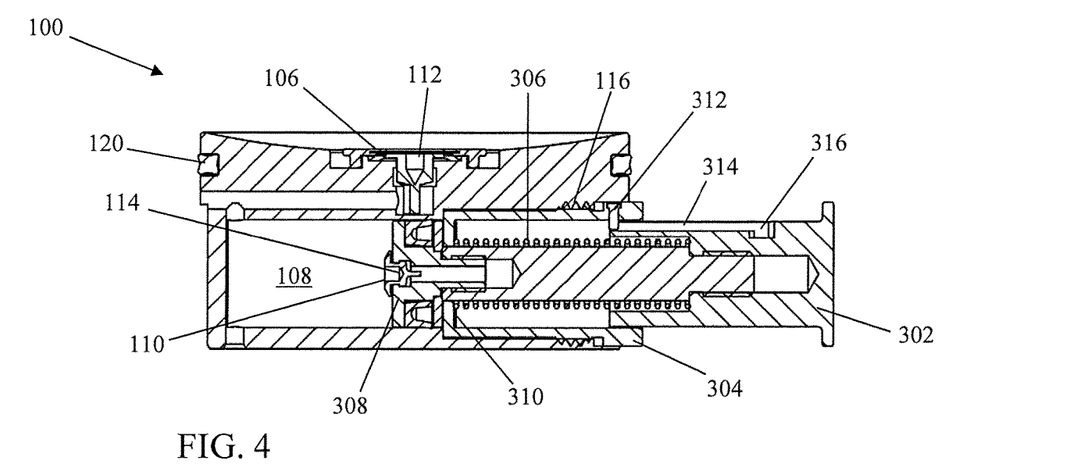
FIG. 4 is a cross-sectional view thereof with the piston in a neutral position.
Figure 5:
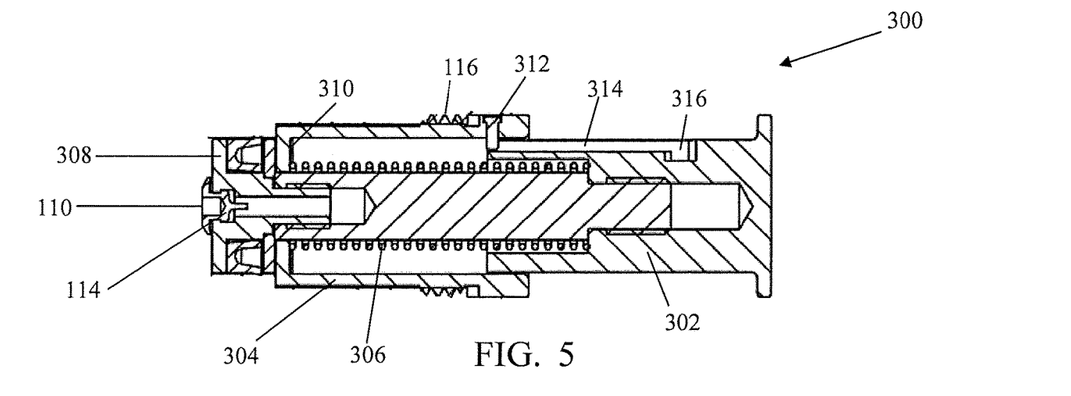
FIG. 5 is a cross-sectional view of the pump mechanism or piston cartridge.

Referring to FIG. 4, a cross-sectional view of the Prosthetic Vacuum Pump 100 is shown with pump mechanism 300 inserted into the body 104. FIG. 5 illustrates a cross-sectional view of the pump mechanism 300 removed.

In some embodiments, the pump mechanism 300 may include a piston 302 and a biasing member 306. The biasing member 306 may be a coil spring, leaf spring, hydraulic apparatus, or other suitable mechanism for storing force to create a reciprocating relationship between the piston 302 and the inner chamber 108.

In other embodiments, the pump mechanism 300 may include only a piston 302 configured to reciprocate within an inner chamber 108. In embodiments without a biasing member 306, the piston 302 may be manually reciprocated within the inner chamber 108 to create the vacuum.

In one exemplary embodiment, the piston 302 is secured within a housing 304 and a spring 306 is connected to the piston 302 and housing 304 to facilitate and control a reciprocating movement of the piston 302. The piston head 308 on one end of the piston 302 extends out of the housing 304 and into an inner chamber 108, or vacuum chamber. By way of example, one end of the spring 306 connects to the piston 302 and the other end of the spring 306 abuts or connects to an end wall or flange 310 on an opposing end of the housing 304. In one exemplary embodiment, when the piston 302 moves in a first direction, the spring 306 compresses, and the piston head 308 moves within the inner chamber 108. In this first direction, air is forced out of the inner chamber 108 via an exhaust port 110. Then, the spring 306 returns to its neutral position moving the piston 302 in a second direction. Movement in the second direction draws air out of the prosthetic socket with the intake port 106 and into the inner chamber 108. In one exemplary embodiment, the Vacuum Pump 100 includes an intake valve 112 and an exhaust valve 114 located at the intake port 106 and exhaust port 110, respectively. The intake valve 112 and the exhaust valve 114 may be one-way valves.

In some embodiments, the exhaust port 110 and exhaust valve 114 are located on the piston head 308. When the piston 302 is depressed, air in the inner chamber 108 is forced through the exhaust port 110 and released to atmosphere. By way of example, air in the inner chamber 108 may move through the exhaust port 110 through the piston 302, into the housing 304, and be expelled to atmosphere from the housing 304.

In embodiments including the piston 302 and spring member 306 within a self-contained housing 304, the pump mechanism 300 may be removed from the body 104 of the Pump 100. By way of example, the pump mechanism 300 may be removably attached to the body 104 by threaded attachment 116.

In an exemplary method using the Prosthetic Vacuum Pump 100, a pump mechanism 300 has a predetermined level of vacuum that it can apply within the cavity 202. The predetermined level of vacuum is a maximum level of vacuum that can be drawn by the pump mechanism 300. Different pump mechanisms or piston cartridges 300 may have springs 306 with a different length, tension, or constant that results in a predetermined level of vacuum. For example, a first pump mechanism 300 may only draw a vacuum of 7 inches of mercury (inHg) and a second pump mechanism 300 may draw 20 inHg.

In one exemplary method, a user may begin drawing the vacuum with a pump mechanism 300 that is configured to draw a larger amount of air from the socket 200 to create and secure the prosthetic more quickly. Then, the user may install another pump mechanism or cartridge 300 that draws a lower predetermined level of vacuum to wear throughout the day for adjusting the fit of the socket 200 as volume of the residual limb decreases throughout the day requiring an increased or re-applied vacuum to maintain a secure fit of the prosthetic on the residual limb.

In some embodiments, the pump mechanism 300 may include a locking mechanism 312. The locking mechanism 312 maintains the piston 302 in a depressed position which makes the Vacuum Pump 100 less bulky and able to be more easily worn under pants. In one exemplary embodiment, the locking mechanism may be a pin 312 located on the housing 304 with a corresponding locking channel 314 such that when the piston 302 is depressed, the user can make a small rotation of the piston 302 to engage the locking pin 312 with a locking slot 316.

Figure 6:
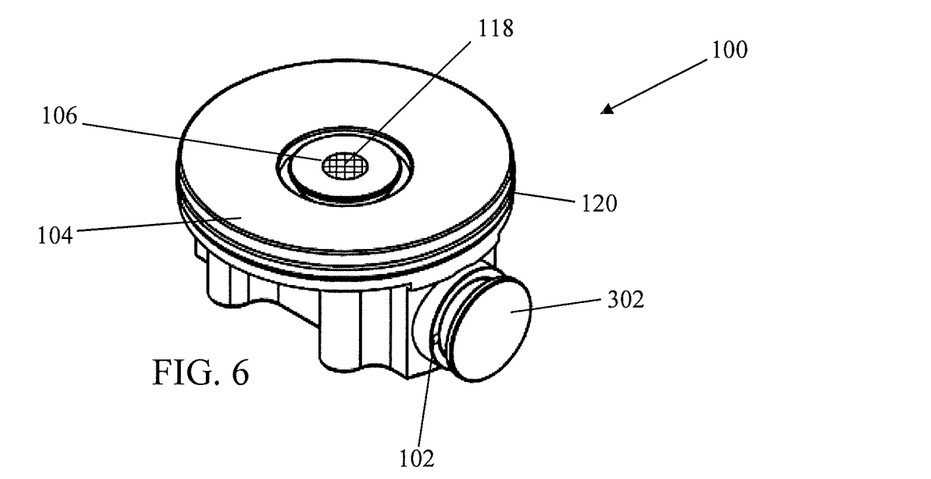
FIG. 6 is a perspective view of the Prosthetic Vacuum Pump with piston in depressed position.
Figure 7:
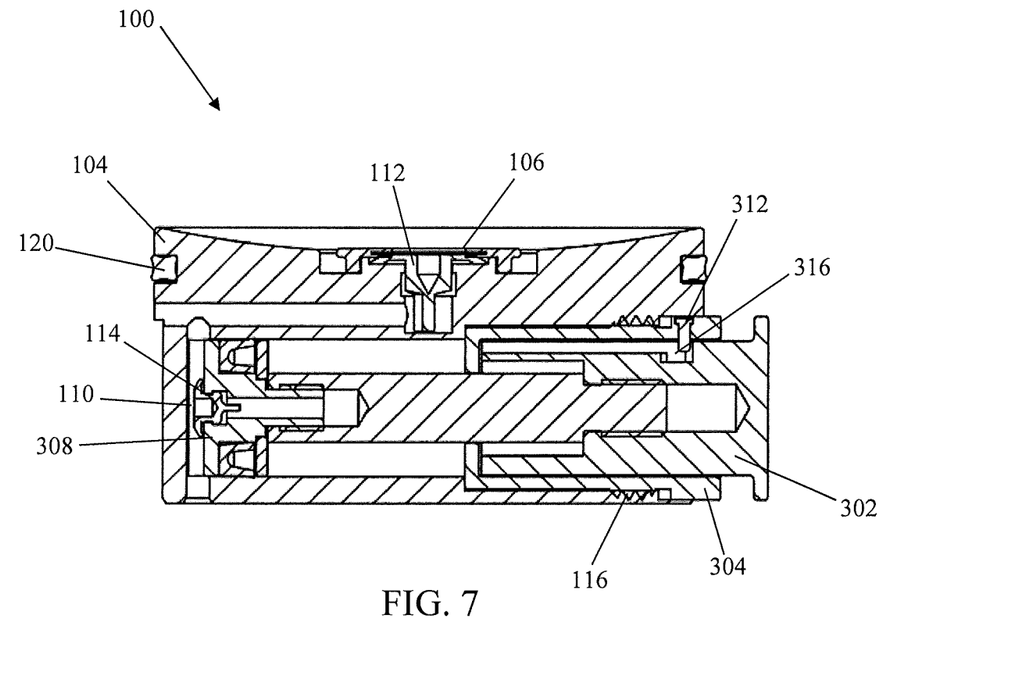
FIG. 7 is a cross-sectional view thereof with the piston depressed.

Referring to FIGS. 6 and 7, the piston 302 may be depressed and secured by the locking mechanism 312.

In another exemplary embodiment, a filter 118 (shown in FIG. 6) may be placed over the intake port 106. The filter 118 may be inline to prevent debris, dirt, dust, or lint from the prosthetic socks or other foreign objects from blocking the intake valve 112 or causing a leak in vacuum. By way of example, the filter 118 may be a stainless steel mesh with plastic over-molded to allow for fastening over the intake port 106.

In another exemplary method, the Vacuum Pump 100 may be affixed to a socket 200 without a prosthetic limb 204 attached. Proper blood flow to a recent wound or amputation is important for the body's healing process. This is especially important in a recently amputated limb. Another benefit of the elevated vacuum is retaining or drawing blood flow to a wounded area in a post-operative setting. Wounds need blood flow to heal but a residual limb in use with a prosthesis has blood pushed away from the most important area. The continual application of an elevated vacuum at the site of amputation will provide healing benefits to the post-op patient. In this application, the Vacuum Pump 100 may be used to draw blood to an area of a body part or residual limb to facilitate healing.

Figure 8:
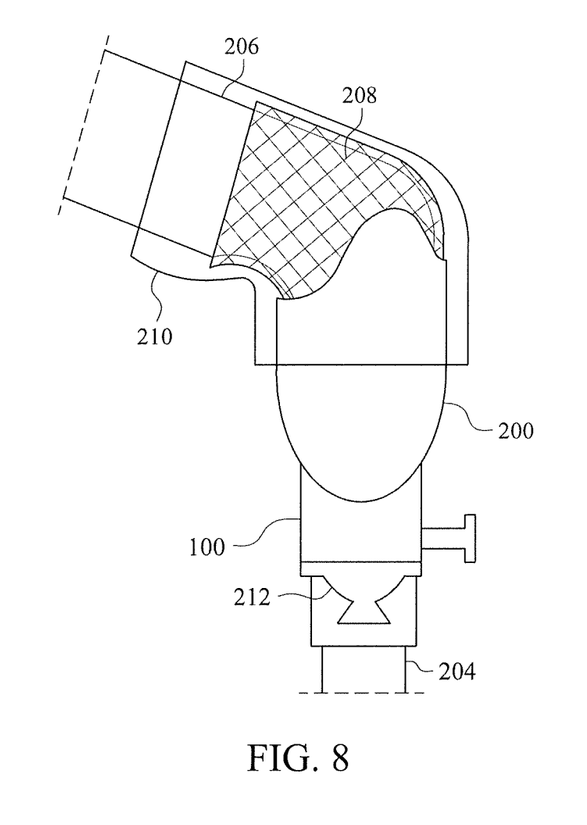
FIG. 8 illustrates an exemplary prosthetic device incorporating the Vacuum Pump attached to a residual limb with a liner interface and sealing sleeve.

Referring to FIG. 8, a prosthetic device incorporating Vacuum Pump 100 is shown in use on a residual limb with a liner interface 206 and sealing sleeve 208. In this exemplary embodiment, a prosthetic device includes the Vacuum Pump 100 integrated into the distal end of the prosthetic socket 200. On the bottom of the Vacuum Pump 100, an integral mounting interface 212 secures the prosthetic socket 200 to a prosthetic limb 204. In this embodiment, a user applies the liner interface 208 to the residual limb 206 and then inserts the lined residual limb into the prosthetic socket 200. Vacuum is obtained in the prosthetic socket 200 by the sealing sleeve 210 creating a seal on the residual limb 206 that is above the prosthetic socket 200. The liner interface 208 may be made from silicone, urethane, or thermoplastics with an outer layer of fabric. The liner interface 208 wicks air away from the residual limb 206 allowing the Vacuum Pump 100 to draw vacuum over the entire prosthetic socket 200.

Figure 9:
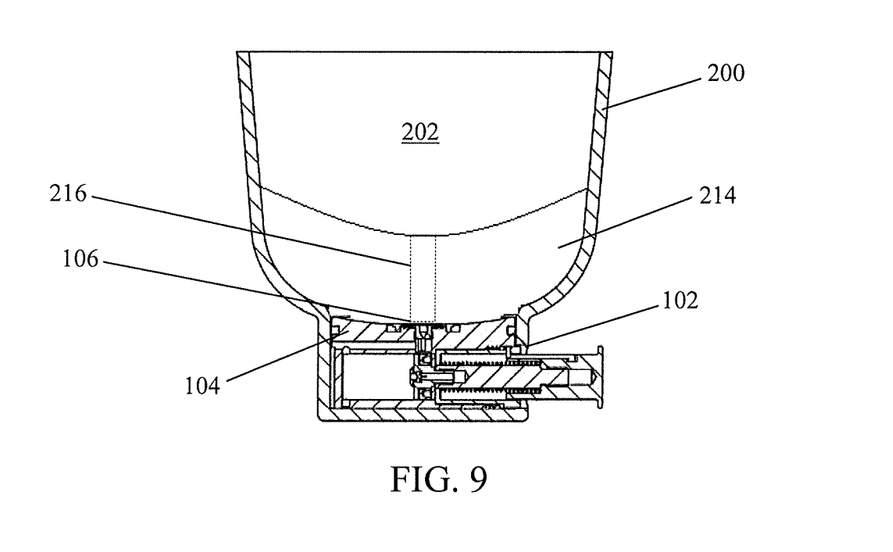
FIG. 9 illustrates another exemplary embodiment of a prosthetic socket including a distal end pad.

Referring to FIG. 9, a prosthetic socket 200 is shown with a distal end pad 214. The distal end pad 214 may be used with the Prosthetic Vacuum Pump 100 by placing the distal end pad 214 on the top surface of the body 104. The distal end pad 214 includes a hole 216 for air to be drawn out of the prosthetic socket cavity 202 by the Prosthetic Vacuum Pump 100.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the embodiments described herein are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A device to create an elevated vacuum in a prosthetic socket, the device comprising:
    a body secured to the distal end of the prosthetic socket, the body and the prosthetic socket forming a cavity to receive a residual limb, and the body having a top surface, an inner chamber, an intake port, and an exhaust port;
    a manually-operated pump mechanism removably attached to the body and having a piston, a housing, and a biasing member, the piston reciprocating within the housing to create a predetermined level of vacuum in the prosthetic socket;
    an opening of the intake port on the top surface of the body is in fluid communication between the cavity and the inner chamber; and
    an opening of the exhaust port on the piston is in fluid communication between the inner chamber and atmosphere;
    whereby movement of the piston in a first direction expels air from the inner chamber to atmosphere through the exhaust port and movement of the piston in a second direction pulls air from the cavity into the inner chamber through the intake port creating an elevated vacuum in the cavity.

2. The device of claim 1, wherein the biasing member is configured to move the piston in the second direction to return the piston to a starting position.

3. The device of claim 1, wherein the pump mechanism further comprises a spring to control the reciprocating movement of the piston within the housing, the spring attached to the piston and the housing.

4. The device of claim 1, further comprising a locking mechanism configured to secure the piston in a depressed position.

5. The device of claim 4, wherein the locking mechanism comprises a locking slot located on and running lengthwise along the piston and a locking pin affixed to and extending out from the housing.

6. The device of claim 1, further comprising a second pump mechanism having a second predetermined level of vacuum, the second pump mechanism removably attached to the body to draw the second level of vacuum in the cavity, and the second predetermined level of vacuum is different from the predetermined level of vacuum.

7. The device of claim 1, further comprising an intake valve located on the opening of the intake port to prevent back flow of air into the prosthetic socket.

8. The device of claim 1, further comprising an exhaust valve located on the opening of the exhaust port to prevent air from the atmosphere entering the inner chamber.

9. The device of claim 1, further comprising the distal end of the prosthetic socket is affixed to and extends upward from the top surface of the body to create the cavity.

10. The device of claim 9, further comprising a distal end pad situated on the top surface of the body, the distal end pad having a hole aligned with the intake port.

11. A device to create an elevated vacuum in a prosthetic socket, the device comprising:
    a cavity in the prosthetic socket configured to receive a residual limb;
    a body having a top surface affixed to a distal end of the prosthetic socket, an inner chamber, an intake port in fluid communication between the cavity and the inner chamber, and an exhaust port in fluid communication between the atmosphere and the inner chamber;
    a first manually-operated pump mechanism removably attached to the body in the inner chamber, the first manually-operated pump mechanism having a housing, a piston reciprocating within the housing, and a first spring having a first spring constant;
    wherein the first manually-operated pump mechanism draws a first predetermined level of vacuum in the cavity; and
    a second manually-operated pump mechanism having a second spring with a second spring constant;
    wherein the second manually-operated pump mechanism draws a second predetermined level of vacuum in the cavity; and
    the first manually-operated pump mechanism and the second manually-operated pump mechanism interchangeably insert into the body.

12. The device of claim 11, wherein movement of the piston in a first direction expels air from the inner chamber to atmosphere through the exhaust port, and movement of the piston in a second direction draws air out of the cavity into the inner chamber through the intake port.

13. The device of claim 11, further comprising the exhaust port located in the piston and air in the inner chamber is expelled through the piston.

* * * * *